US012144772B2

(12) United States Patent
Gregg et al.

(10) Patent No.: US 12,144,772 B2
(45) Date of Patent: Nov. 19, 2024

(54) TOTAL ENERGY SHAPING CONTROL METHODS AND DEVICES FOR POWERED ORTHOSIS

(71) Applicant: BOARD OF REGENTS, THE UNIVERSITY OF TEXAS SYSTEM, Austin, TX (US)

(72) Inventors: Robert D. Gregg, Allen, TX (US); Ge Lv, Dallas, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 1259 days.

(21) Appl. No.: 16/615,495

(22) PCT Filed: May 21, 2018

(86) PCT No.: PCT/US2018/033586
§ 371 (c)(1),
(2) Date: Nov. 21, 2019

(87) PCT Pub. No.: WO2018/217593
PCT Pub. Date: Nov. 29, 2018

(65) Prior Publication Data
US 2020/0085603 A1  Mar. 19, 2020

Related U.S. Application Data

(60) Provisional application No. 62/509,339, filed on May 22, 2017.

(51) Int. Cl.
*A61H 1/02* (2006.01)
*A61B 5/00* (2006.01)
(Continued)

(52) U.S. Cl.
CPC ......... *A61H 1/0262* (2013.01); *A61B 5/0057* (2013.01); *A61B 5/11* (2013.01);
(Continued)

(58) Field of Classification Search
CPC .......... A61H 1/00; A61H 1/02; A61H 1/0237; A61H 1/024; A61H 1/0244; A61H 1/0255;
(Continued)

(56) References Cited

U.S. PATENT DOCUMENTS

2010/0114329 A1\*  5/2010  Casler ................. B62D 57/032
                                                     623/24
2010/0125229 A1   5/2010  Rudolph et al.
(Continued)

FOREIGN PATENT DOCUMENTS

WO   WO 2016/130745   8/2016
WO   WO 2017/105996   6/2017

OTHER PUBLICATIONS

Murray et al., Towards the Use of a Lower Limb Exoskeleton for Locomotion Assistance in Individuals with Neuromuscular Locomotor Deficits, 2012, 34th Annual International Conference of the IEEE EMBS (Year: 2012).\*

(Continued)

*Primary Examiner* — Colin W Stuart
(74) *Attorney, Agent, or Firm* — Parker Highlander PLLC (57) ABSTRACT

Total energy shaping control methods and devices for powered orthosis for controlling the device to counteract forces exerted on the person including inertial forces.

32 Claims, 5 Drawing Sheets

(51) Int. Cl.
*A61B 5/11* (2006.01)
*A61F 5/01* (2006.01)
*A61H 3/00* (2006.01)
*B25J 9/00* (2006.01)
*B25J 9/12* (2006.01)

(52) U.S. Cl.
CPC ............ *A61B 5/112* (2013.01); *A61B 5/6812* (2013.01); *A61B 5/6828* (2013.01); *A61B 5/6829* (2013.01); *A61F 5/0102* (2013.01); *A61H 1/024* (2013.01); *A61H 1/0244* (2013.01); *A61H 1/0266* (2013.01); *A61H 3/00* (2013.01); *B25J 9/0006* (2013.01); *B25J 9/126* (2013.01); *A61F 2005/0155* (2013.01); *A61H 2201/1207* (2013.01); *A61H 2201/1472* (2013.01); *A61H 2201/5061* (2013.01); *A61H 2201/5064* (2013.01); *A61H 2201/5069* (2013.01); *A61H 2201/5084* (2013.01); *A61H 2205/10* (2013.01); *A61H 2205/12* (2013.01); *A61H 2230/625* (2013.01)

(58) Field of Classification Search
CPC .. A61H 1/0259; A61H 1/0262; A61H 1/0266; A61H 1/0274; A61H 1/0277; A61H 1/0281; A61H 1/0285; A61H 2230/62; A61H 2230/625; A61H 2205/10; A61H 2205/102; A61H 2205/106; A61H 2205/108; A61H 2205/12; A61H 3/00; A61H 2201/12; A61H 2201/1207; A61H 2201/1215; A61H 2201/1472; A61H 2201/164; A61H 2201/50; A61H 2201/5053; A61H 2201/5058; A61H 2201/5061; A61H 2201/5064; A61H 2201/5069; A61H 2201/5079; A61H 2201/5084; B25J 9/0006; B25J 9/126; A61B 5/0057; A61B 5/11; A61B 5/112; A61B 5/6812; A61B 5/6828; A61B 5/6829; A61F 2/70; A61F 2/60; A61F 2/604; A61F 2/605; A61F 2/64; A61F 2/66; A61F 2/68; A61F 2002/701; A61F 2002/607; A61F 2002/608; A61F 2002/6836; A61F 2002/7625; A61F 2002/7635; A61F 2002/7645

See application file for complete search history.

(56) References Cited

U.S. PATENT DOCUMENTS

| | | |
|---|---|---|
| 2012/0109025 A1* | 5/2012 | Weinberg ............ A63B 24/0087 601/5 |
| 2012/0283845 A1 | 11/2012 | Herr et al. |
| 2013/0296746 A1 | 11/2013 | Herr et al. |
| 2014/0142474 A1 | 5/2014 | McBean et al. |
| 2015/0257902 A1* | 9/2015 | Martin .................. A61F 2/6607 623/47 |
| 2015/0374573 A1 | 12/2015 | Horst et al. |

OTHER PUBLICATIONS

Holm et al., Kinetic Energy Shaping for Gait Regulation of Underactuated Bipeds, Sep. 3-5, 2008, 17th IEEE International Conference on Control Applications, 1232-1238 (Year: 2008).*

Lv et al., Orthotic Body-Weight Support Through Underactuated Potential Energy Shaping with Contact Constraints, Dec. 15-18, 2015, 2015 IEEE 54th Annual Conference on Decision and Control, 1483-1490 (Year: 2015).*

PCT International Preliminary Report on Patentability issued in International Application No. PCT/US2018/033586, mailed on Dec. 5, 2019.

PCT International Search Report and Written Opinion issued in International Application No. PCT/US2018/033586, mailed on Aug. 24, 2018.

* cited by examiner

TOTAL ENERGY SHAPING CONTROL METHODS AND DEVICES FOR POWERED ORTHOSIS

CROSS-REFERENCE TO RELATED APPLICATIONS

This application is a national phase application under 35 U.S.C. § 371 of International Application No. PCT/US2018/033586, filed May 21, 2018, which claims priority to U.S. Provisional Patent Application Ser. No. 62/509,339 filed May 22, 2017, the contents of each of which are incorporated herein by reference.

GOVERNMENT LICENSE RIGHTS

This invention was made with government support under DP2HD080349 awarded by the National Institutes of Health and under 1652514 awarded by the National Science Foundation. The government has certain rights in the invention.

BACKGROUND INFORMATION

State of the Art in Powered Lower-Limb Exoskeletons

The majority of assistive exoskeletons are designed to rigidly track time-based kinematic patterns, which forces users to follow specific joint positions during walking. Despite the fact that these exoskeletons have shown promising results in assisting individuals with spinal cord injury (SCI), critical barriers still exist in the control technology that limits their overall adaptability. Kinematic control method is limited to replicating the normative joint kinematics associated with one specific task and user at a time [1]. These pre-defined trajectories cannot adjust to continuously varying activities or changes in user behavior associated with learning during gait rehabilitation. These devices also have to accurately recognize the user's intent to transition from one task-dependent controller to another [2, 3], which is hard to realize in practice [4]. Multiple task-specific controllers also require more tuning time for each user [5, 6], and this procedure will continue as users make progress in gait training. Moreover, rigid position control methods require little or no contribution from the human user [7]. This may make sense for SCI subjects but not for people with partial or full volitional control of their limbs. For example, able-bodied persons or individuals post stroke should be allowed to adjust their joint kinematics during the learning process based on corrections from the therapist. Lower-limb exoskeletons require a novel task-invariant control paradigm that provides kinematic adaptability. As discussed further below, energy shaping is proposed as the basis for this new paradigm.

State of the Art in Energy-Shaping Control

Energy shaping is a control method that alters the dynamical characteristics of a mechanical system [8-12]. Prior work on energy shaping has primarily focused on stabilizing mechanical systems at equilibrium points. Through control action, the closed loop system can be forced to behave like another system with beneficial properties such as provable stability or other enhanced performance. In one of the closest fields to exoskeleton control design, energy shaping has been applied to simple biped models to create natural, efficient gaits based on passive dynamics [13-17]. These approaches leverage the existence of unactuated "passive walking" gaits, which use only momentum and gravity to propel forward motion down a shallow slope [18-22]. The method of controlled symmetries shapes potential energy (rotating the gravity vector) to map passive gaits to actuated gaits on arbitrary slopes [23, 24]. Kinetic energy shaping can then regulate walking speed [25-27]. Through interconnection and damping assignment, the authors designed a passivity-based controller in [28] to perform different walking gaits on a compass-gait biped model. Additionally, by using energy shaping techniques, planar gaits can be mapped to 3D space to create stable walking gaits [17, 29].

Despite this rich body of work, practical limitations have prevented energy shaping from being adopted in human-like bipedal or wearable robots. Prior work has been limited to simple toy models where the matching conditions, are tractable. The matching conditions are sets of nonlinear partial differential equations (PDEs) that dictate the achievable forms of a system's closed-loop energy. While these equations can be trivially solved with the case of full actuation (i.e., the number of actuators equals the number of degrees of freedom (DOFs)), they can be quite challenging to satisfy when the system is underactuated (i.e., the number of actuators is less than the number of DOFs). In [26], the authors leveraged the method proposed in [18] to convert the matching conditions into a set of linear PDEs that are easier to solve.

Although these linear PDEs have simpler forms compared to the nonlinear PDEs, they are still very challenging to solve even for a simple compass-gait biped model. The use of more realistic human-like biped models will bring tremendous difficulties in solving the matching conditions, which prevents this method being applied to design controllers for multi joint exoskeletons. Wearable robots for human locomotion also require a new energy shaping control method that explicitly accounts for the presence of environmental and human interaction. Prior work used simple toys models with point feet or flat feet with a single contact model, often assuming full actuation. Humans are not point-footed or flat-footed walkers. In human walking, contact varies from heel to toe resulting in multiple periods of underactuation, which cannot be captured by state-of-art energy shaping methods. Moreover, it was previously unknown how to incorporate human interaction forces into the energy shaping framework for applications in wearable robots, especially when the human actively contributes to the walking gait.

SUMMARY

Exemplary embodiments of the present disclosure include an orthosis device comprising a first support member, a second support member, an actuator, a controller and a plurality of sensors configured to measure a plurality of parameters. In particular embodiments, the plurality of parameters includes an angle between the first support member and the second support member, and an orientation of the first support member or the second support member. In some embodiments, the actuator is configured to apply a torque to the first or second support member, and the controller is configured to calculate a plurality of forces exerted on the person and orthosis device. In specific embodiments, the plurality of forces include an inertial force and a gravitational force, and the plurality of forces are calculated based on the angle between the first support member and the second support member and based on the orientation of the first support member or the second support member. In certain embodiments, the controller is configured to control the torque applied by the actuator, and the torque applied by the actuator is controlled to counteract the plurality of forces exerted on the person and device.

In particular embodiments, the plurality of sensors includes an inertial measurement unit (IMU) coupled to the first support member or the second support member. In some embodiments, the plurality of sensors includes a joint encoder configured to measure the angle between the first support member and the second support member. In specific embodiments, the joint encoder is an optical encoder or a magnetic encoder.

In certain embodiments, the controller comprises a closed-loop total energy shaping control system. In particular embodiments, the torque applied by the actuator is kinetically controlled via a nonlinear control method. In some embodiments, the actuator comprises an electric motor, and the controller is configured to vary an electric current to the electric motor. In specific embodiments, the first support member is configured to be coupled to a shin of a person, the second support member is configured to be coupled to a thigh of a person, and the actuator is configured to vary the angle between the first support member and the second support member.

In certain embodiments, the first support member is configured to be coupled to a thigh of a person, and the second support member is configured to be coupled to a hip of a person, and the actuator is configured to vary the angle between the first support member and the second support member. In particular embodiments, the first support member is configured to be placed under a foot of a person, the second support member is configured to be coupled to a shin of a person, and the actuator is configured to vary the angle between the first support member and the second support member. In certain embodiments, the plurality of sensors comprises a first sensor in the first support member configured to measure a force in a ball area of the foot of the person. In some embodiments, the plurality of sensors comprises a second sensor in the first support member configured to measure a force in a heel area of the foot of the person. In specific embodiments, the actuator comprises an electric motor coupled to a gearbox and a first sprocket, the orthosis device comprises a second sprocket coupled to the first support member, and the orthosis device comprises a belt coupling the first sprocket and the second sprocket. Certain embodiments further comprise a reaction torque sensor coupled to the gearbox. In particular embodiments, the gearbox comprises a planetary gear transmission, and wherein the reaction torque sensor is configured to measure torque at an end of the planetary gear transmission.

In some embodiments, the orthosis device comprises: an electric motor, a first sprocket, a second sprocket, a belt and a gearbox, where the electric motor is coupled to the first sprocket, the belt couples the first sprocket and the second sprocket, and the gearbox is located inside the second sprocket. In specific embodiments, the gearbox is configured to be coupled to a joint of a person. In certain embodiments, the orthosis device comprises an electric motor and a gearbox, where the electric motor is directly coupled to the gearbox. In particular embodiments, the gearbox is a single-stage planetary gearbox. In some embodiments, the gearbox is configured to be coupled to a joint of a person.

Certain embodiments include a method for controlling an orthosis device coupled to a person, where the method comprises measuring a plurality of parameters, where the orthosis device comprises a first support member, a second support member, an actuator and a controller, and the plurality of parameters includes an angle between the first support member and the second support member, and an orientation of the first support member or the second support member. In particular embodiments, the method comprises applying a torque to one of the plurality of support members via the actuator, and controlling the torque applied via the actuator. In some embodiments, the torque applied via the actuator is controlled to counteract the plurality of forces exerted on the orthosis device, and torque applied via the actuator is not controlled to direct the orthosis device in a pre-determined pattern of motion.

In certain embodiments, the orientation of the first support member or the second support member is measured via an inertial measurement unit (IMU). In particular embodiments, the angle between the first support member and the second support member is measured via an optical encoder. In some embodiments, the actuator controls the torque via a closed-loop total energy shaping control system. In specific embodiments, the torque is kinetically controlled via a nonlinear control method. In certain embodiments, the actuator comprises an electric motor, and wherein the controller varies an electric current to the electric motor to control the torque applied via the actuator. In particular embodiments, the first support member is coupled to a shin of a person, the second support member is coupled to a thigh of a person, and the actuator varies the angle between the first support member and the second support member. In some embodiments, the first support member is placed under a foot of a person; the second support member is coupled to a shin of a person; and the actuator varies the angle between the first support member and the second support member. In specific embodiments, the plurality of sensors comprises a first sensor in the first support member, and the first sensor in the first support member measures a force in a ball area of the foot of the person. In certain embodiments, the plurality of sensors comprises a second sensor in the first support member, and the second sensor in the first support member measures a force in a heel area of the foot of the person.

In particular embodiments, the actuator comprises an electric motor coupled to a gearbox and a first sprocket, the orthosis device comprises a second sprocket coupled to the first support member, and the orthosis device comprises a belt coupling the first sprocket and the second sprocket. In specific embodiments, the orthosis device comprises a reaction torque sensor coupled to the gearbox. In certain embodiments, the gearbox comprises a planetary gear transmission, and wherein the reaction torque sensor measures torque at an end of the planetary gear transmission.

In the present disclosure, the term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will be apparent to those skilled in the art from this detailed description.

DETAILED DESCRIPTION OF ILLUSTRATIVE EMBODIMENTS

Exemplary embodiments of the present disclosure constitute a paradigm shift from task-specific, kinematic control approaches to task-invariant, energetic control approaches needed for lower-limb exoskeletons to assist their human users across varying locomotor activities. Exemplary embodiments of the present invention introduce a new methodology for task-invariant control of powered orthotic devices based on energy shaping, where the parameters and/or formula for the human body's energy are altered in closed loop to achieve more desirable dynamics (see e.g. conceptual example in FIG. 1).

Figure 1:
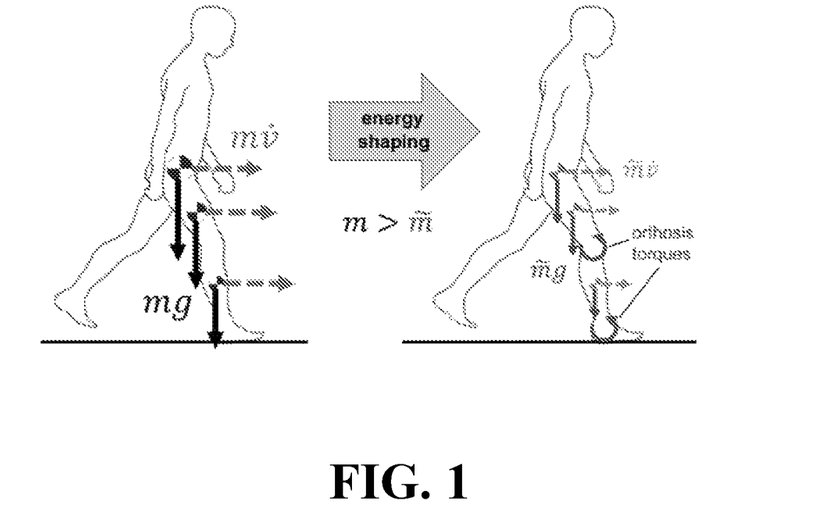
FIG. 1 illustrates a schematic diagram for shaping body energy through a powered knee-ankle exoskeleton according to exemplary embodiments of the present disclosure.

FIG. 1 illustrates a conceptual diagram for shaping body energy through a powered knee-ankle exoskeleton. In this example, exoskeleton torques reduce the effect of body/limb masses on the user's mechanical energy and thus dynamics. Shaping these mass parameters in the potential energy results in smaller perceived forces from gravity (solid vectors), whereas shaping them in the kinetic energy allows the user to accelerate or decelerate with less muscular effort (dashed force vectors).

Motivated by the work in [31], this application leverages the holonomic contact constraints encountered during human walking and generalizes the classical energy shaping matching condition for constraint-free Lagrangian dynamics (used in [31]) to the case of Lagrangian dynamics with holonomic contact constraints [32, 33]. By modeling generalized dynamics instead of lower-dimensional contact-specific dynamics, the inventors transform the conventional Lagrangian dynamics into the equivalent constrained dynamics (ECD) that have fewer (or possibly zero) DOFs. Based on these constrained dynamics, the matching conditions become easier to satisfy. Because the inventors show the matching proof without making assumptions on system and actuator dimensions, the proposed framework can be used to design controllers for different applications. By shaping potential energy from wearable actuators, torques can be generated to counteract gravity in the vertical direction. This control action yields so-called body-weight support, which offloads the perceived weight of the user's lower extremities and center of mass. Similarly, kinetic energy shaping can reduce the perceived mass and inertia of the human-robot system to generate assistance in all directions of motion. Because this control method augments the joint dynamics rather than tracking joint kinematics, the exoskeleton determines how the joints should move instead of where they move. Therefore, the assistance is invariant of the task and the preferred kinematics of the user.

Modeling the Biped

Figure 2:
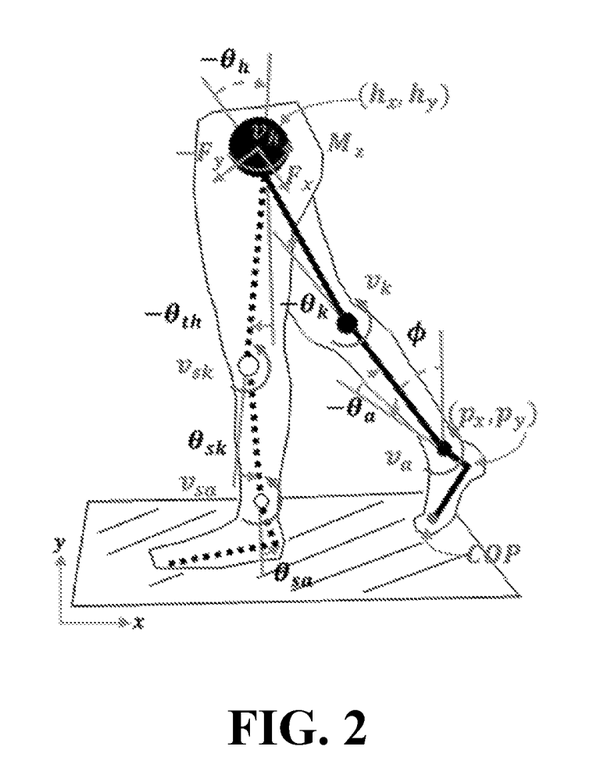
FIG. 2 illustrates a kinematic model of the human body and the exoskeleton.

The biped is modeled as a kinematic chain with respect to an inertial reference frame (IRF, to be specified later) shown in FIG. 2. FIG. 2 illustrates a kinematic model of the human body and the exoskeleton(s). The stance leg is shown in solid black and the swing leg (just before impact) in dashed black. For controlling a unilateral exoskeleton, the inventors separately model the stance and swing legs. The stance leg is modeled as a kinematic chain from the IRF, which is defined at the stance heel during heel and flat foot contact versus the stance toe during toe contact. As for the swing leg, the inventors choose the hip as a floating base for the swing leg's kinematic chain. For simulations of the full biped model, the angle $\theta_h$ is defined as the hip angle between the stance and swing thighs, and the solid arcs around the joints indicate the human muscle inputs.

Depending on whether the exoskeleton is unilateral or bilateral, the inventors choose to model the stance and swing legs separately (unilateral case [32, 33]) or the entire lower body as a kinematic chain from the stance foot to the swing foot (bilateral case [34]). By explicitly modeling contact constraints in the dynamics, the equations of motion (EOM) can be expressed as $$M(q)\ddot{q}+C(q,\dot{q})+N(q)+A(q)^T\lambda=\tau, \quad (1)$$

where $M(q)\in\mathbb{R}^{n\times n}$ is the positive-definite inertia matrix, $C(q,\dot{q})\in\mathbb{R}^{n\times n}$ is the Coriolis/centrifugal matrix, and $N(q)=\mathbb{R}^{n\times 1}$ denotes the gravitational forces vector. The configuration vector is given as $q=(\theta_x, \theta_y, \theta_{ab}, q_s^T)^T\in\mathbb{R}^n$, where $\theta_x$ and $\theta_y$ are the Cartesian coordinates with respect to the IRF, $\theta_{ab}$ is an absolute angle defined with respect to the vertical axis, and the shape vector $q_s\in\mathbb{R}^{n-3}$ contains joint angles based on the biped model (to be specified in the simulation section). The matrix $A(q)^T\in\mathbb{R}^{n\times c}$ is the constraint matrix defined as the gradient of the holonomic constraint functions (see next section), and c is the number of contact constraints depending on the contact condition. The Lagrange multiplier $\lambda$ is calculated using the method in [5, 35] as $$\lambda = \hat{\lambda} + \bar{\lambda}\sigma, \text{ where}$$

$$\hat{\lambda} = W(q)(\dot{A}(q)\dot{q} - A(q)M(q)^{-1}C(q,\dot{q})\dot{q} - A(q)M(q)^{-1}N(q)),$$

$$\bar{\lambda} = W(q)A(q)M(q)^{-1}, \text{where}$$

$$W(q) = (A(q)M(q)^{-1}A(q)^T)^{-1}. \tag{2}$$

Because the human body and exoskeleton are considered together, the torque $\tau = \tau_{hum} \pm \tau_{exo}$ at the right-hand side of (1) comprises the human input terms $\tau_{hum} = B(q)v + J(q)^T F$ and the exoskeleton input $\tau_{exo} = B(q)u$. The mapping matrix $B(q) \in \mathbb{R}^{n \times p}$ maps both the human muscular torques $v \in \mathbb{R}^p$ and the exoskeleton actuator torques $u \in \mathbb{R}$ into the dynamics. Without loss of generality, one can assume $B(q)$ takes the form of $[0_{p \times (n-p)}, I_{p \times p}]^T$. The force vector $F = (F_x, F_y, M_z)^T \in \mathbb{R}^{3 \times 1}$ in $\tau_{hum}$ denotes the interaction forces between the stance model and the swing leg model, where $(F_x, F_y)^T$ and $M_z$ indicate the two linear forces and a moment in the sagittal plane, respectively. The forces F are mapped into the dynamics by the body Jacobian matrix $J(q)^T \in \mathbb{R}^{n \times 3}$. Note that for bilateral exoskeleton models, the interaction forces F are internal to the dynamics of the complete kinematic chain and hence will not show up as an external input (i.e., F=0).

Holonomic Contact Constraints

In the previous section, the inventors explicitly modeled contact in the dynamics without specifying the choice of contact constraints. In this section, the inventors define the general form of holonomic contact constraints encountered during the single-support period of human walking, which are expressed as relations between the position variables:

$$a(q_1, q_2, \ldots, q_c) = 0_{c \times 1}, \tag{3}$$

where $q_i$ denotes the i-th element of the configuration vector q. The single-support period can be separated into heel contact, flat foot, and toe contact phases, based on which appropriate holonomic contact constraints can be defined as in FIG. 3. There are c=2 constraints for heel contact and toe contact whereas flat foot has c=3. As discussed further below, the proposed framework is able to accommodate arbitrary numbers of contact constraints. In this paper, the inventors assume the constraint matrix A(q) has the constant form $$A(q) = \nabla_q a(q_1, q_2, \ldots, q_c) = [I_{c \times c} 0_{c \times (n-c)}] \tag{4}$$

This constant form (that is, $\dot{A}=0$) can be achieved by defining the IRF at the stance toe during toe contact and the stance heel during heel and flat foot contact.

Figure 3:
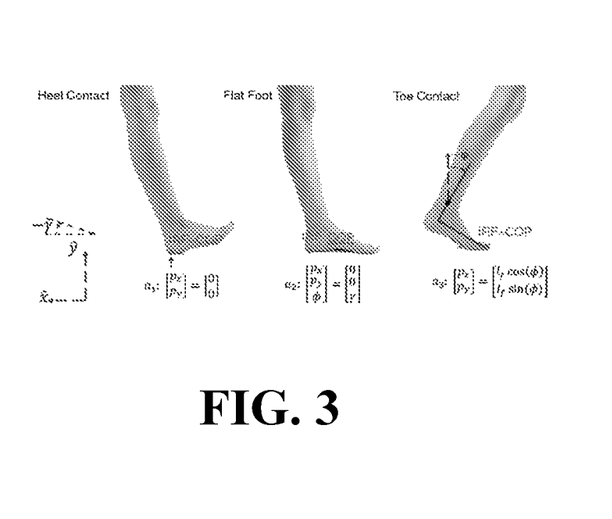
FIG. 3 illustrates a diagram of heel contact condition (left), flat foot condition (center), toe contact condition (right) during the single-support period of human locomotion.

FIG. 3 illustrates heel contact condition (left), flat foot condition (center), toe contact condition (right) during the single-support period of human locomotion. For simulation purposes, it is assumed the biped is walking on a slope with angle $\gamma$.

Equivalent Constrained Dynamics

Instead of modeling a different dynamical system for each phase, the inventors will introduce a shaping framework which can accommodate any holonomic contact constraints (and the resulting unactuated DOFs) that could occur during various locomotor tasks. This generalized framework shows what terms can and cannot be shaped with each contact constraint. The inventors start the proposed approach by plugging expressions for A(q) and $\lambda$ into (1) to obtain the equivalent constrained dynamics that have fewer (possibly zero) unactuated DOFs compared to the generalized dynamics (1) without constraints. Following the procedure in [34], the equivalent constrained form of (1) is expressed as $$M_\lambda \ddot{q} + C_\lambda \dot{q} + N_\lambda = B_\lambda V + J_\lambda^T F + B_\lambda u, \tag{5}$$

where $M_\lambda = M$, $$C_\lambda = (I - A^T W A M^{-1})C + A^T W \dot{A},$$

$$N_\lambda = (I - A^T W A M^{-1})N,$$

$$B_\lambda = (I - A^T W A M^{-1})B,$$

$$J_\lambda^T = (I - A^T W A M^{-1})J^T. \tag{6}$$

Given the open-loop dynamics (5), the inventors define the desired closed-loop ECD as $$\tilde{M}_\lambda \ddot{q} + \tilde{C}_\lambda \dot{q} + \tilde{\tau}_{hum}, \tag{7}$$

where $\tilde{M}_\lambda = \tilde{M}$ is the mass/inertia matrix in the closed-loop ECD and is assumed to be positive-definite. The remaining terms in (7) are given by $$\tilde{C}_\lambda = (I - A^T \tilde{W} A \tilde{M}^{-1})\tilde{C} + A^T \tilde{W} \dot{A},$$

$$\tilde{N}_\lambda = (I - A^T \tilde{W} A \tilde{M}^{-1})\tilde{N},$$

$$\tilde{B}_\lambda = (I - A^T \tilde{W} A \tilde{M}^{-1})\tilde{B},$$

$$\tilde{J}_\lambda^T = (1 - A^T \tilde{W} A \tilde{M}^{-1})\tilde{J}^T,$$

$$\tilde{W} = (A \tilde{M}^{-1} A^T)^{-1}, \tag{8}$$

where $\tilde{C}$ and $\tilde{N}$ are the dynamics terms of (1) in closed loop.

The inventors denote the closed-loop human input vector as $\tilde{\tau}_{hum} = \tilde{B}_\lambda v + \tilde{J}_\lambda^T F$ but make no assumptions on the human inputs v and F. Because the human joint input v and the interaction forces F are not easily measured in practice, the inventors choose the closed-loop mappings $\tilde{B}$ and $\tilde{J}^T$ such that v and F disappear from the exoskeleton control law and the matching condition is satisfied. Based on the matching proof in the appendix, $\tilde{B}$ and $\tilde{J}$ are given as $$\tilde{B} = \begin{bmatrix} I_{c \times c} & 0_{c \times (n-c)} \\ 0_{(n-c) \times c} & \tilde{M}_4 M_4^{-1} \end{bmatrix} B, \quad \tilde{J}^T = \begin{bmatrix} I_{c \times c} & 0_{c \times (n-c)} \\ 0_{(n-c) \times c} & \tilde{M}_4 M_4^{-1} \end{bmatrix} J^T. \tag{9}$$

These terms immediately satisfy the matching condition and alter the way that the human joint inputs v and interaction forces F enter the closed-loop system dynamics. Given (9), the inventors proved in the Appendix A that the bottom-right p×p submatrix of M and the rows in N that correspond to the actuated coordinates can be shaped via control. The corresponding control law that brings (5) into (7) is then given as $$u = (B_\lambda^T B_\lambda)^{-1} B_\lambda^T [C_\lambda \dot{q} + N_\lambda - M_\lambda \tilde{M}_\lambda^{-1}(\tilde{C}_\lambda \dot{q} + \tilde{N}_\lambda)]. \tag{10}$$

Simulation of Energy-Shaping Control on a Human-Like Biped

The inventors now wish to study the efficacy of energy shaping control during simulated walking with the full biped model in FIG. 2. This requires the inventors to consider the coupled dynamics of the two legs [5]. The full biped is modeled as a kinematic chain with respect to the IRF defined at the stance heel with the configuration vector $q = (\theta_x, \theta_y, \theta_{ab}, q_s^T)^T = (p_x, P_y, \phi, \theta_a, \theta_k, \theta_h, \theta_{sk}, \theta_{sa})^T \in \mathbb{R}^8$. We pick $(\theta_x, \theta_y)^T = (p_x, p_y)^T$ as the Cartesian coordinates of the stance heel and $\theta_{ab} = \phi$ as the stance heel angle defined with respect to the vertical axis. In the shape vector $q_s = (\theta_a, \theta_k, \theta_h, \theta_{sk}, \theta_{sa})^T$, $\theta_a$ and $\theta_{sa}$ are the angles of the stance and swing ankle, $\theta_k$ and $\theta_{sk}$ are angles of the stance and swing knee, and $\theta_h$ is the hip angle between the stance and swing thighs.

Impedance Control for Human Inputs

In order to predict the effects of the proposed control approach, the inventors first constructed a human-like, stable walking gait in simulation. According to the results in [36], a simulated 7-link biped can converge to a stable, natural-looking gait using joint impedance control. The control torque of each joint can be constructed from a spring-damper coupled with phase-dependent equilibrium points [37]. The inventors adopt this control paradigm to generate dynamic walking gaits that preserve the ballistic swing motion [38] and the energetic efficiency down slopes [39], which are characteristic of human locomotion. The inventors assume that the human has input torques at the ankle, knee and hip joints. For simplicity, the inventors keep the human impedance parameters constant instead of having a different set of parameters with respect to each phase of stance as in [37]. The human input vector $\tau_{hum}$ for the full biped model is given as $$\tau_{hum}=[0_{1\times 3}, v_a, v_k, v_h, v_{sk}, v_{sa}]^T \in \mathbb{R}^{8\times 1}, \quad (11)$$

where $v_j$ is the human torque for joint $j \in \{a, k, h, sk, sa\}$ and is given as $$v_j = -K_{pj}(q_j - \bar{q}_j) - K_{dj}\dot{q}_j, \quad (12)$$

where $K_{pj}, K_{dj}, q_j, \bar{q}_j$ respectively correspond to the stiffness, viscosity, actual angle, and equilibrium angle of joint j.

Hybrid Dynamics

Biped locomotion can be modeled as a hybrid dynamical system which includes continuous and discrete dynamics. Impacts happen when the swing heel contacts the ground and subsequently when the flat foot impacts the ground. The corresponding impact equations map the state of the biped at the instant before impact to the state at the instant after impact. Note that no impact occurs when switching between the flat foot and toe contact configurations, but the location of the IRF does change from heel to toe in order to maintain a constant constraint matrix A. Based on the method in [5], the hybrid dynamics and impact maps during one step are computed in the following sequence:

1. $M\ddot{q} + C\dot{q} + N + A_{heel}^T \lambda = \tau_{exo} + \tau_{hum}$ if $a_{flat} \neq 0$,
2. $\dot{q}^+ = (I - M^{-1}A_{flat}^T(A_{flat}M^{-1}A_{flat}^T)^{-1})\dot{q}^-$ if $a_{flat} = 0$,
3. $M\ddot{q} + C\dot{q} + N + A_{flat}^T \lambda = \tau_{exo} + \tau_{hum}$ if $|c_p(q,\dot{q})| < l_f$,
4. $\dot{q}^+ = \dot{q}^-, (q(1)^+, q(2)^+)^T = \mathcal{G}$ if $|c_p(q,\dot{q})| = l_f$,
5. $M\ddot{q} + C\dot{q} + N + A_{toe}^T \lambda = \tau_{exo} + \tau_{hum}$ if $h(q) \neq 0$,
6. $(q^+, \dot{q}^+) = \Delta(q^-, \dot{q}^-)$ if $h(q) = 0$, where $M \in \mathbb{R}^{8\times 8}$, $C \in \mathbb{R}^{8\times 8}$, and $N \in \mathbb{R}^8$ are the dynamics terms of the full biped model. The terms $A_{heel}, A_{flat}$ and $A_{toe}$ denote the constraint matrices for the heel contact, flat foot, and toe contact conditions depicted in FIG. 3, and the superscripts "−" and "+" indicate values before and after each impact. The term $\mathcal{G} = (l_f \cos(\gamma), l_f \sin(\gamma))^T$ models the change in IRF for foot length $l_f$. The vector $c_p(q,\dot{q})$ is the COP defined with respect to the heel IRF calculated using the conservation law of momentum. The ground clearance of the swing heel is denoted by $h(q)$, and $\Delta$ denotes the swing heel ground-strike impact map derived based on [40]. The aforementioned sequence of continuous and discrete dynamics repeats after a complete step, that is, phase 6 switches back to phase 1 for the next step.

Shaping Strategies

The main mechanical tasks that require energy during human walking are (i) supporting the body's weight during stance, (ii) driving the body's center of mass (COM) against inertia, (iii) swinging the legs, and (iv) maintaining balance. A percentage of the subject's weight is typically offloaded using an overhead body weight support (BWS) harness during gait rehabilitation to reduce the muscular force required for the first task. While the harness can offload the human weight that needs to be supported by the stance leg, there is no straightforward way to offload the human swing leg's weight. Not being able to compensate for swing leg mass can have consequences such as the foot drop phenomenon in individuals post stroke. A second limitation of the conventional BWS strategy is that COM and leg inertia compensation is not possible. Braking forces at heel strike decelerate the COM, which again needs to be accelerated during the drive phase. A study of the independent effects of weight and mass on the metabolic cost of walking [41] found that driving the COM against inertia accounts for up to 50% of the total metabolic cost. Kinetic energy-shaping assistance from an exoskeleton could potentially reduce this metabolic cost, and prior work [42] indicates that inertia compensation can counteract the side effects of the exoskeleton inertia on human legs during walking.

These facts motivate us to compensate the limb inertia and body weight in the shapeable parts of ECD. Therefore, we choose $\tilde{M}_4$ and $\tilde{N}$ by scaling the limb moments of inertia in $M_4 \in \mathbb{R}^{p\times p}$ and the gravity constant in the shapeable part of N:

$$\tilde{M}_4 = \tilde{M}_D + \tilde{M}_I, \quad (13)$$

$$\tilde{N} = [N_{1,n-p}^T, \tilde{N}_{n-p+1,n}^T]^T = [N_{1,n-p}^T, \mu N_{n+p+1,n}^T]^T, \quad (14)$$

where $\tilde{M}_D \in \mathbb{R}^{p\times p}$ and $\tilde{M}_I \in \mathbb{R}^{p\times p}$ are matrices that correspond to the translational and rotational portions of kinetic energy of $\tilde{M}_4$, respectively [43].

Compensating for Limb Inertia and Providing BWS

In this section, the inventors present the simulation results with a specific total energy shaping strategy: Compensating for lower-limb inertia via kinetic energy shaping and providing BWS via potential energy shaping. As used herein, the term "total energy shaping control system" is understood to be a control system that compensates for inertial forces via kinetic energy shaping and compensates for gravitational forces via potential energy shaping. As a case study, the inventors want to simulate shaping strategies for a human wearing a bilateral hip-knee-ankle exoskeleton. The dynamics of this biped model coincides with the simulation model and hence will not be introduced again. For this bilateral biped model, compensating all limb inertia terms in $M_4 \in \mathbb{R}^{5\times 5}$ and scaling the gravity terms in the shapeable parts of N indicates $$\tilde{M}_4 = \tilde{M}_D + \tilde{M}_I = M_D + \kappa \cdot M_I, \quad (15)$$

$$\tilde{N} = [N_{1,n-p}^T, \tilde{N}_{n-p+1,n}^T]^T = [N_{1,3}^T, \mu N_{4,8}^T]^T. \quad (16)$$

For notational purposes, $0 \leq \kappa < 1$ indicates we are providing $(1-\kappa) \cdot 100\%$ support for compensating limb inertia, whereas $\kappa > 1$ indicates we are adding $(\kappa - 1) \cdot 100\%$ virtual limb inertia in closed loop. Analogously, $0 < \mu < 1$ indicates the exoskeleton is providing $(1-\mu) \sim 100\%$ BWS ($\tilde{g} < g$), while $\mu > 1$ indicates the exoskeleton is providing $(\mu - 1) \cdot 100\%$ negative BWS ($\tilde{g} > g$).

Gait Characteristics

To compare the changes in gait characteristics, the inventors show the step length, step linear velocity, and step time periods recorded during simulation with different shaping strategies in Table 1. From this table, one can see that compensating body mass and/or limb inertia in the shapeable dynamics with potential energy shaping and/or total energy shaping decreases the step length as well as the step linear velocity but increases the time periods spent for each step. In contrast, adding virtual body mass and/or limb inertia increases step length and step linear velocity but reduces time interval for each step. For the case of kinetic energy shaping only ($\kappa=0$), step length and walking speed decreased because of a contraction in the hip orbit (i.e., reduced hip extension causes a shorter step [44]). A similar observation holds for the case of $\kappa=1.2$. These simulation results indicate that different shaping strategies can be chosen based on training goals to promote different gait characteristics.

TABLE 1

Compensating lower-limb inertia: Step length and step linear velocity recorded in simulation with different shaping strategies.

| Strategies | Step length [m] | Step linear velocity [m/s] |
|---|---|---|
| Passive ($\mu = \kappa = 1$) | 0.5259 | 1.0113 |
| PE ($\mu = 1.1$) | 0.5379 | 1.1049 |
| PE ($\mu = 1.05$) | 0.5352 | 1.0554 |
| PE ($\mu = 0.95$) | 0.5281 | 0.9740 |
| PE ($\mu = 0.9$) | 0.5264 | 0.9492 |
| KE ($\kappa = 2$) | 0.5677 | 1.2598 |
| KE ($\kappa = 1.2$) | 0.5368 | 1.0286 |
| KE ($\kappa = 0.8$) | 0.5259 | 0.9996 |
| KE ($\kappa = 0$) | 0.5114 | 0.9807 |
| Total ($\kappa = 1.2, \mu = 1.2$) | 0.5424 | 1.2044 |
| Total ($\kappa = 0.85, \mu = 0.85$) | 0.5197 | 0.9335 |

Metabolic Cost

Figure 4:
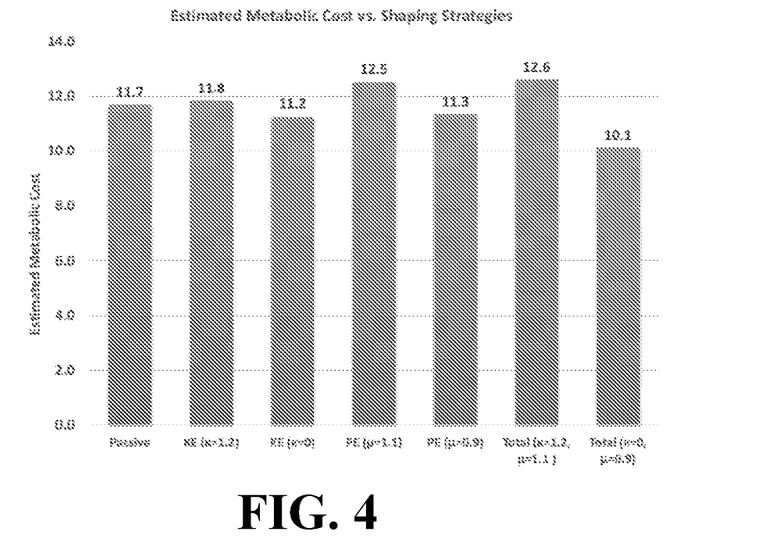
FIG. 4 illustrates a graph of the estimated metabolic costs with different shaping strategies.

A key metric for evaluating an exoskeleton is whether it reduces the human user's metabolic cost of walking [45]. The integral of electromyography (EMG) squared readings from the Soleus and Vastus Lateralis muscles are a good representation of total metabolic cost [46]. Assuming EMG activation is directly related to joint torque production, the authors of [47] proposed a simulation-based metric for metabolic cost $$\alpha_j^2 = \frac{\int_0^T v_j^2(t)dt}{T(mgl)^2} \approx \frac{\sum_{i=1}^{N_T} v_j^2(i)\Delta t}{T(mgl)^2}, \quad (17)$$

where T is the step time period, $N_T$ is the number of timesteps in the simulation, $v_j$ is the joint moment, m is the overall mass of the biped, g is the gravity constant, and l is the length of the biped leg. Therefore, the inventors computed the sum of all human joint costs (17) to estimate the effects of energy shaping on the metabolic cost of walking, where several different conditions are shown in FIG. 4. The numbers on top of each bar in FIG. 4 denote the sum of (17) for all actuated human joints given a certain shaping strategy indicated on the x-axis.

From this figure, one can see that adding 20% virtual limb inertia (KE, $\kappa=1.2$) has minor effects on the metabolic cost compared to the passive gait, whereas compensating all the limb inertia (KE, $\kappa=0$) reduces the metabolic cost. Similarly for the case of potential energy shaping, negative BWS (PE, $\mu=1.1$) increases the biped's metabolic cost, whereas positive BWS (PE, $\mu=0.9$) reduces the overall metabolic cost compared to the passive gait. This meets the inventors' expectation that offloading the weight of a patient makes it easier to practice walking. For total energy shaping, $\kappa=1.2$ and $\mu=1.1$ made the biped consume more metabolic energy than only shaping kinetic energy with $\kappa=1.2$ or potential energy with $\mu=1.1$. When compensating limb inertia in addition to gravity by total energy shaping ($\kappa=0, \mu=0.9$), the biped consumed the least amount of energy compared to all the other cases in FIG. 4. These results suggest that the energy shaping approach could provide meaningful assistance during gait rehabilitation, where a clinician can adjust the scaling factors to actively manipulate human effort.

Mass-Inertia Compensation and BWS

For this strategy, the inventors needed to first find proper ways to define $\tilde{M}_4$ with reduced mass and inertia parameters such that the overall closed-loop inertia matrix $\tilde{M}=\tilde{M}_\lambda$ is positive definite. One interesting property about the inertia matrix is that the mass and inertia terms show up following a "cyclic-like property" as introduced in [48], i.e., the number of links whose parameters show up in the matrix gradually decreases when traversing from the top-left corner to the bottom-right corner of the inertia matrix. This suggests that each "layer" of the matrix carries a different weight in the overall kinetic energy. Motivated by this fact, the inventors came up with a new shaping strategy that scales each layer with a different number $k_i$ as:

$$\tilde{M}_4 = \begin{bmatrix} k_1 \cdot M_{n-p+1,n-p+1} & k_1 \cdot M_{n-p+1,n-p+2} & \cdots & k_1 \cdot M_{n-p+1,n} \\ k_1 \cdot M_{n-p+2,n-p+1} & k_2 \cdot M_{n-p+2,n-p+2} & \cdots & k_2 \cdot M_{n-p+2,n} \\ \vdots & \vdots & \ddots & \vdots \\ k_1 \cdot M_{n,n-p+1} & k_2 \cdot M_{n,n-p+2} & \cdots & k_p \cdot M_{n,n} \end{bmatrix} \in \mathbb{R}^{p \times p}.$$

By defining $\tilde{M}_4$ in this manner, we are respecting the structure of the inertia matrix, hence the choice for each $k_i$ should be more flexible. Now the problem of ensuring $\tilde{M}=\tilde{M}_\lambda>0$ can be formulated as finding possible $K=[k_1, k_2, \ldots, k_p]$ such that the minimum eigenvalue of $\tilde{M}_\lambda$ stays strictly positive, i.e., $$\text{minimum}(eig(\tilde{M}_\lambda)) > 0,$$

$$\text{subject to } \begin{pmatrix} q_j \in [-\frac{\pi}{2}, \frac{\pi}{2}], & j = 1, 2, \ldots, 8 \\ 0 < k_i \leq 1, & i = 1, 2, \ldots, 5 \end{pmatrix}$$

To find solutions for $k_i$ that ensures $\tilde{M}_\lambda$ is positive definite, the inventors used the MATLAB function fmincon and the results are shown in Table 2. Note that the inventors have constrained the range for each joint variable $q_j$ to be within $$[-\frac{\pi}{2}, \frac{\pi}{2}],$$

which is sufficient to cover the range for common locomotor tasks [49]. For the simulation in the next section, the inventors choose parameters from Table 2 to define $\tilde{M}_\lambda$ and use notation from (16) to define $\tilde{N}$.

TABLE 2

Solutions for $k_i$ that ensure $\tilde{M} = \tilde{M}_\lambda$ is positive definite

| $k_1$ | $k_2$ | $k_3$ | $k_4$ | $k_5$ |
|---|---|---|---|---|
| 1 | 1 | 1 | 1 | 0.9 to 0.6 |
| 1 | 1 | 1 | 0.9 | 1 to 0.5 |
| 1 | 1 | 1 | 0.8 | 1 to 0.6 |
| 1 | 1 | 0.9 | 1 | 1 to 0.6 |
| 1 | 1 | 0.9 | 0.9 | 1 to 0.5 |
| 1 | 1 | 0.9 | 0.8 | 1 to 0.5 |
| 1 | 1 | 0.9 | 0.7 | 1 to 0.6 |

As examples, the inventors chose two sets of $k_i$ from Table 2 to define $\tilde{M}_\lambda$ with reduced mass and inertia parameters in $\tilde{M}_4$, i.e., $K_2$=[1, 1, 0.9, 0.8, 0.5] and $K_4$=[1, 1, 0.9, 1, 0.6]. The inventors also picked $K_1$=[1, 1, 1.1, 1.2, 1.5] and $K_3$=[1, 1, 1.1, 1, 1.4] accordingly based on the choices of $K_2$ and $K_4$ to add virtual mass and inertia in the closed loop for comparison purposes. For shaping the potential energy, the inventors selected μ=1.15 and μ=0.85 to provide 15% negative BWS and 15% BWS, respectively.

TABLE 3

Compensating mass and lower-limb inertia: Step length and step linear velocity recorded in simulation with different shaping strategies.

| Strategies | Step length [m] | Step linear velocity [m/s] |
|---|---|---|
| Passive (μ = K = 1) | 0.5259 | 1.0113 |
| KE ($K_1$) | 0.5542 | 1.0238 |
| KE ($K_2$) | 0.4753 | 0.9859 |
| KE ($K_3$) | 0.5595 | 1.0213 |
| KE ($K_4$) | 0.4418 | 1.0027 |
| Total ($K_1$, μ = 1.15) | 0.5725 | 1.1561 |
| Total ($K_2$, μ = 0.85) | 0.4849 | 0.8678 |
| Total ($K_3$, μ = 1.15) | 0.5808 | 1.1498 |
| Total ($K_4$, μ = 0.85) | 0.4710 | 0.8660 |

3.5.1 Gait Characteristics

The inventors recorded the step length and step linear velocities during simulation once steady walking was achieved, where the results are shown in Table 3. One can see that by increasing the mass and inertia parameters in human energetics via kinetic energy shaping ($K_1$ and $K_3$) the biped has longer and faster steps compared to the passive gait, whereas reducing the mass and inertia parameters ($K_2$ and $K_4$) yields shorter and slower steps. With total energy shaping that adds virtual mass and inertia ($K_1$,μ=1.15 and $K_3$,μ=1.15), the biped has even longer and faster steps compared to the case of just shaping the kinetic energy. When the inventors applied total energy shaping to reduce closed-loop energy ($K_2$,μ=0.85 and $K_4$,μ=0.85), although the biped's step length remains close to the case of kinetic energy shaping, the step linear velocity drops drastically. These results reveal the fact that total energy shaping can further affect the biped's step linear velocity. To provide assistance for human locomotion, we can decide the most appropriate shaping strategies to promote certain gait characteristics based on the requirements of clinicians and therapists.

3.5.2 Metabolic Cost

Figure 5:
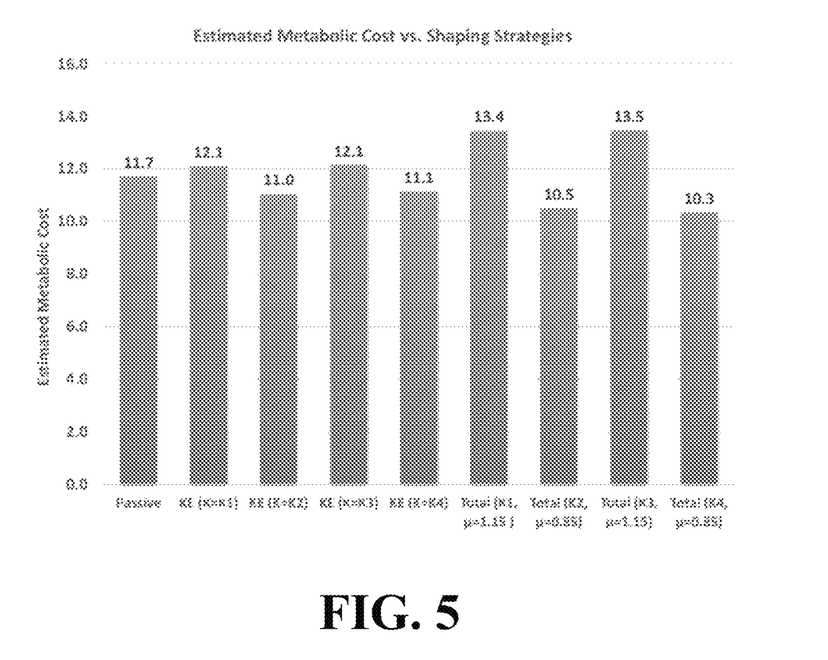
FIG. 5 illustrates a graph of the estimated metabolic costs with different shaping strategies.

The inventors again used (17) to estimate the metabolic cost during walking, where the results are shown in FIG. 5. In FIG. 5, the estimated metabolic costs with different shaping strategies. Numbers on top of each bar denotes the sum of (17) for all actuated human joints given a certain shaping strategy indicated on the x-axis.

For the case of kinetic energy shaping, the inventors can infer that adding virtual mass and inertia ($K_1$ and $K_3$) increases the overall metabolic cost while reducing virtual mass and inertia ($K_2$ and $K_4$) decreases the metabolic cost compared to the original gait. Similarly, total energy shaping with $K_1$,μ=1.15 and $K_3$,μ=1.15 increases the metabolic cost while metabolic cost reduction can be seen for the other two total energy shaping cases ($K_2$,μ=0.85 and $K_4$,μ=0.85). It is worth noting that the total energy shaping cases again rendered the greatest changes in the metabolic cost (both increment and reduction), which further illustrated the benefits of shaping the total energy compared to just shaping the kinetic energy. Comparing results from both FIG. 4 and FIG. 5, we can see that shaping mass and inertia terms renders greater effects on the metabolic cost compared to shaping just the lower-limb inertia, hence we can shape the mass terms in practice to further reduce the human metabolic cost during gait training.

Experimental Results

Feedback Control System

Figure 6:
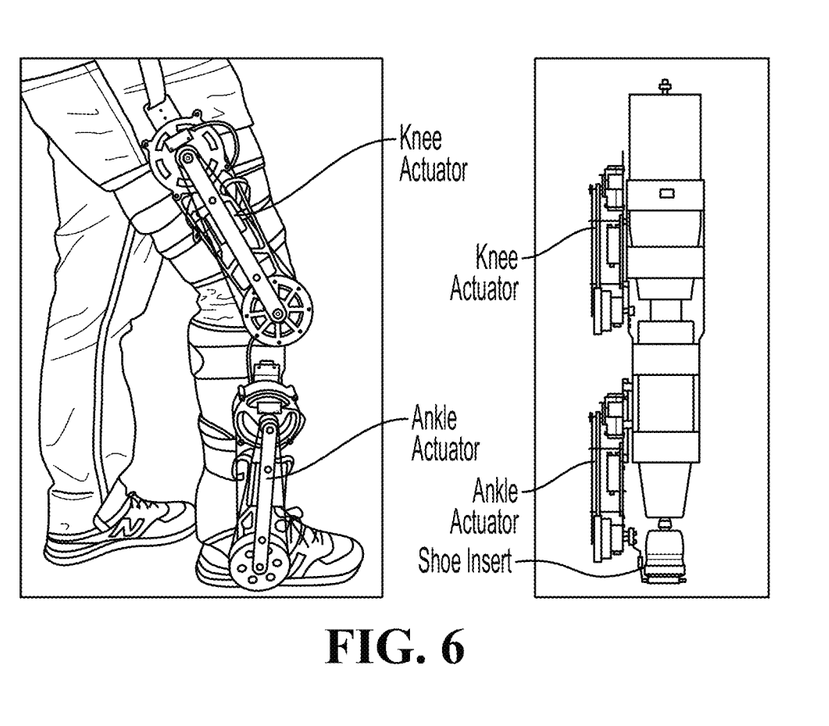
FIG. 6 illustrates front and side views of a powered knee-ankle exoskeleton according to exemplary embodiments of the present disclosure.

In this section, the inventors briefly introduce the system structure of the powered knee-ankle exoskeleton used for experimental implementation [50], where the rendering and the actual untethered device are shown in FIG. 6 are shown in side and front views, respectively. The two actuator modules are attached to a knee-ankle-foot orthotic brace to drive the knee and ankle joints. Torque is transferred to the human ankle through a carbon fiber shoe insert. The embodiment shown in FIG. 6 comprises an electric motor coupled to a first sprocket, and further includes a belt coupling the first and second sprocket. In addition, the embodiment shown in FIG. 6 includes a gearbox inside the second sprocket, where the gearbox is coupled to the joint. Certain exemplary embodiments may also comprise a motor directly coupled to a single-stage planetary gearbox coupled to the joint (in lieu of a belt).

Figure 7:
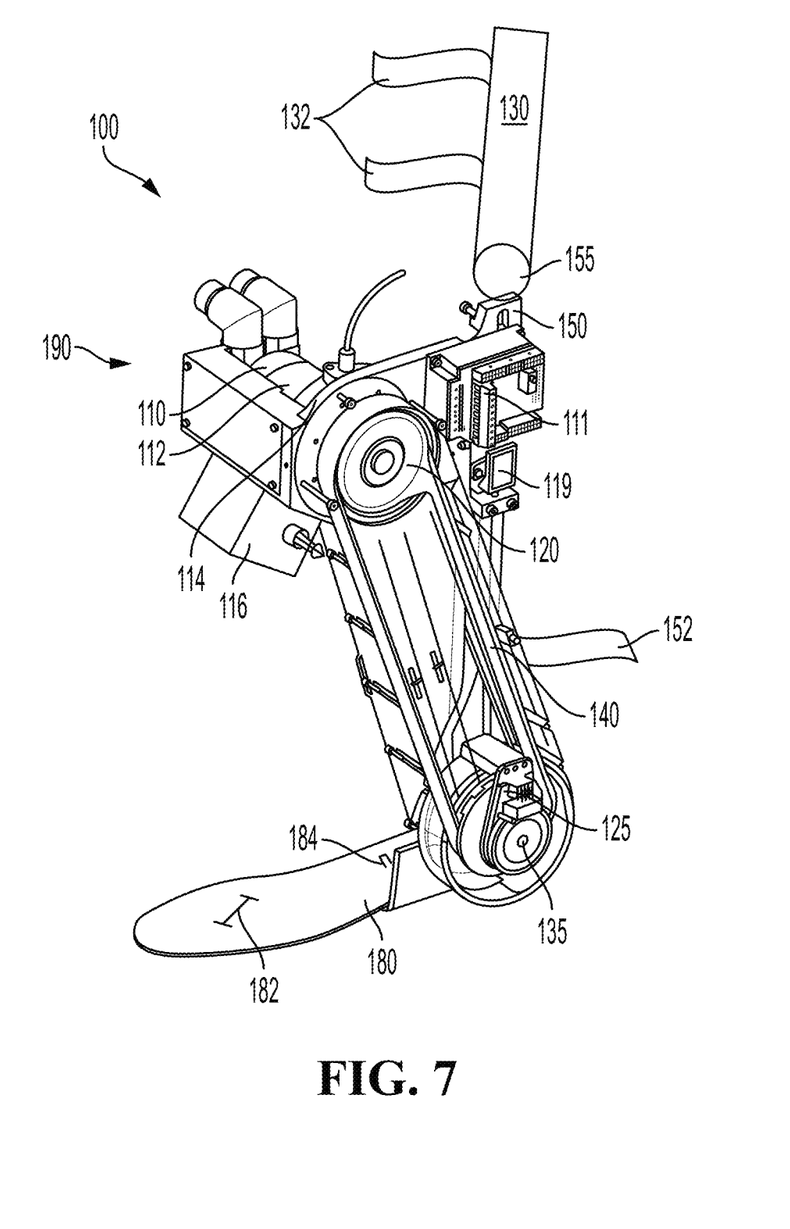
FIG. 7 illustrates a schematic view of a device according to exemplary embodiments of the present disclosure.

Referring now to FIG. 7, another view of an exemplary orthosis (also referred to herein as an orthopedic or orthosis device) is provided. In this embodiment, device 100 is configured as a powered ankle-foot orthosis (PAFO). An overview of device 100 will be presented initially, followed by a more detailed description of the device and its operation. It is understood that device 100 shown in FIG. 7 is merely an exemplary embodiment, and that other embodiments may comprise different components or a different configuration of components, including for example, powered knee-ankle orthosis, powered hip-knee-ankle orthosis, and bilateral powered hip-knee-ankle exoskeleton (i.e., both legs). The embodiment shown in FIG. 7 includes a single actuator system, and it is understood that other embodiments (e.g. the powered knee-ankle device shown in FIG. 6) may comprise one or more additional actuator systems similar to the system shown in FIG. 7 and discussed below.

The embodiment shown in FIG. 7 comprises an actuator 190, an upper support member 130, and an intermediate support 150 member coupled to a lower support member 180. In this embodiment, upper support member 130 may be coupled to a user's thigh area via straps 132, while intermediate support member 150 can be coupled to a user's shin area via straps 152. Upper support member 130 and intermediate support member 150 can be coupled via a pivoting joint 155, and lower support member 180 can be coupled to a user's foot (e.g. proximal to an insole in the user's shoe). In this embodiment actuator 190 comprises a motor 110 coupled to a gearbox 112.

In the embodiment shown in FIG. 7, motor 110 and gearbox 112 are also coupled to a driver sprocket 120 and a driven sprocket 125 via a belt 140. In certain embodiments, belt 140 may be configured as a timing belt or a chain or any flexible member configured to transfer relative rotational motion from driver sprocket 120 to driven sprocket 125.

In addition, motor 110 may optionally be coupled to a torque sensor 114 and torque sensor amplifier 116. Device 100 further comprises a motor controller 111 and an inertial measurement unit (IMU) 119. In the embodiment of FIG. 7, device 100 also comprises a ball force sensor 182 and a heel sensor 184 coupled to lower support 180 as well as a joint encoder 135 coupled to driven sprocket 125.

In a particular embodiment, motor 110 may be configured as a permanent magnetic synchronous motor (PMSM) and gearbox 112 may be configured as a two stage planetary gear transmission (e.g. TPM 004X-031x-lx01-053B-W1-999, Wittenstein, Inc.). In specific embodiments, belt 140 may also be configured as a poly chain GT Carbon timing belt (e.g. 8MGT 720, Gates Industry, Inc.). Such a configuration can provide the desired torque outputs and can be used to move the actuator's weight closer to the user's center of mass, which can minimize the metabolic burden of the added weight [19].

In certain embodiments of device 100 with an overall transmission ratio of 43.71:1, an efficiency of 0.9, and a motor peak torque of 1.29 Nm, the maximum output torque that actuator 190 can achieve is 50 Nm. In addition, actuator 190 can provide 288 W peak power, which should be sufficient for normal human walking speed under the control algorithm disclosed herein. The combination of a high torque PMSM with a low ratio transmission can minimize backdrive torque and provide comfort to the user.

To achieve accurate torque control performance, motor 110 can be configured as a PMSM with distributed winding, which has sinusoidal back-EMF [20]. Such a configuration can be utilized to reduce the torque ripple and to produce smoother torque output. In a particular embodiment, controller 111 may be configured as a field oriented motor controller (e.g. GSol-Gut-35/100, Elmo Motion Control, Inc.). Such a configuration has a lower response time and torque ripple compared to trapezoidal motor control [21]. In certain embodiments, Hall sensors and a resolver can be coupled to motor 110 to obtain accurate position feedback for controller 111.

Given the requirements of the proposed algorithm, the user's gait phase, ankle angle, and absolute shank angle can be measured by encoder 135, and inertial measurement unit (IMU) 119. In particular, encoder 135 can measure the angle between support member 180 (coupled to the user's foot) and intermediate support member 150 (coupled to a user's lower leg/shin area). IMU 119 is coupled to intermediate support member 150 in a fixed manner such that IMU 119 can measure the orientation and velocity of intermediate support member 150.

Optionally, force sensors 182 and 184 (e.g. FlexiForce A301, Tekscan, Inc.) can be embedded into lower support member 180 which can be configured as an insole which is placed beneath the user's foot for detecting the phase of gait, e.g., stance vs. swing. In exemplary embodiments, force sensors 182 and 184 can be placed within the normal COP trajectory to provide precise readings, where force sensor 182 can be placed under the ball of the foot, while force sensor 184 can be placed under the heel.

In certain embodiments, lower support member 180 can be produced on a Connex 350 3D printer and made from a rubber-like polyjet photopolymer. In a particular embodiment, encoder 135 is configured as an optical incremental encoder (e.g., 2048 CPR, E6-2048-250-IE-S-H-D-3, US Digital, Inc.), which can be used to obtain the ankle angle. In addition, IMU 119 may be configured as model number 3DM-GX4-25-RS232-SK1, LORD MicroStrain, Inc. and installed on intermediate support member 150 to obtain the absolute shank angle (e.g. the absolute angle of intermediate support member 150. Particular embodiments may include a safety button that must be held continuously by the user to power device 100, i.e., an enable signal. The user could release the button to disable the device 100 at any point during use, e.g., if balance was the lost.

In the embodiment shown, torque sensor 114 is configured as a reaction torque sensor (e.g., TPM 004+, Wittenstein, Inc.) located between a casing for actuator 190 and intermediate support member 150 to measure the real torque output from actuator 190. Information from torque sensor 114 can be used to reduce the actuator torque error caused by the nonlinear transmission efficiency, the variable motor torque constant, and the backdrive torque.

As disclosed herein, exemplary embodiments of device 100 comprise a control system that provides bodyweight support (BWS) for a user. The use of device 100 can prove beneficial for people who have retained partial control of their motor skills, including for example those who have sustained a stroke and other neurological injury. Persons using device 100 are provided with BWS during conventional gait retraining to help them produce the coordinated muscle activities needed for walking. Device 100 can also be used to augment the performance of able-bodied users, e.g., offloading the weight of the user's body or backpack to minimize metabolic burden in soldiers.

Installing torque sensor 114 at the end of gearbox 112, instead of at the end of the belt 140, avoids additional mass at the ankle joint. By measuring the torque on the case of actuator 190, instead of the output shaft, a non-contact torque sensor can be avoided. This is beneficial since noncontact torque sensors are usually more expensive, larger in size, and heavier than the adopted reaction torque sensor.

Figure 8:
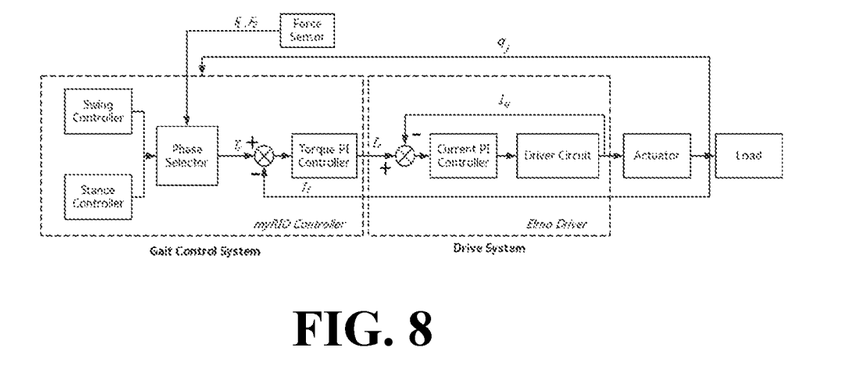
FIG. 8 illustrates a schematic block diagram of a torque control system according to exemplary embodiments of the present disclosure.

The control system of the powered knee-ankle exoskeleton consists of two parts: a high-level gait control system and a low-level actuator drive system, where the block diagram of the whole control system is shown in FIG. 8. In FIG. 8, $q_j$ represents joint angles, $F_1$ and $F_2$ are ground reaction forces, $T_r$ is the reference torque, $T_f$ is the measured output torque, $I_r$ is the reference current, and $I_q$ is the motor's active current [51]. The phase selector switches between the stance and swing controllers, which produce the torque references. The actuator drive system contains two PI control loops. The inner loop is the current PI controller which regulates the motor's current. The optional outer loop is the torque PI controller to compensate for the actuator's torque tracking error.

The gait control system monitors the key variables of the user's gait using an inertial measurement unit (IMU) and two joint encoders (knee and ankle) to compute the energy shaping control torque command. The actuator drive system then drives the actuator to track this torque command from the gait control system. The force sensors were installed on the shoe insert to detect whether the human leg is in stance or swing phase. The actuator output torque is determined by the reference motor current, which is regulated by a Proportional-Integral (PI) control loop by the motor driver (the inner loop in FIG. 8).

As an example case study, the total energy shaping control strategy was implemented on the knee actuator of the exoskeleton in FIG. 6. A healthy, male adult subject was recruited for the experiment according to a protocol approved by the University of Texas at Dallas Institutional Review Board. The exoskeleton was securely strapped to the subject's right leg. The experimental task involved a series of sit-stand-sit (STS) repetitions. STS is an activity of daily living that is often difficult to perform for mobility impaired individuals [53]. For comparison, the exoskeleton was configured to either 1) potential energy shaping (P.E.) mode or 2) total energy shaping (P.E.+K.E.) mode. The subject performed 4-5 repetitions of STS transitions with each mode. In order to maintain consistency, the chair position and height were fixed for all trials and were set such that the subject's knee angle was approximately 90 degrees when he was fully seated. The subject was asked to perform the STS transitions at a pace that felt comfortable to him (self-paced). Several practice trials were performed with each mode for the purpose of acclimation to the device; these were excluded from the analysis.

Figure 9:
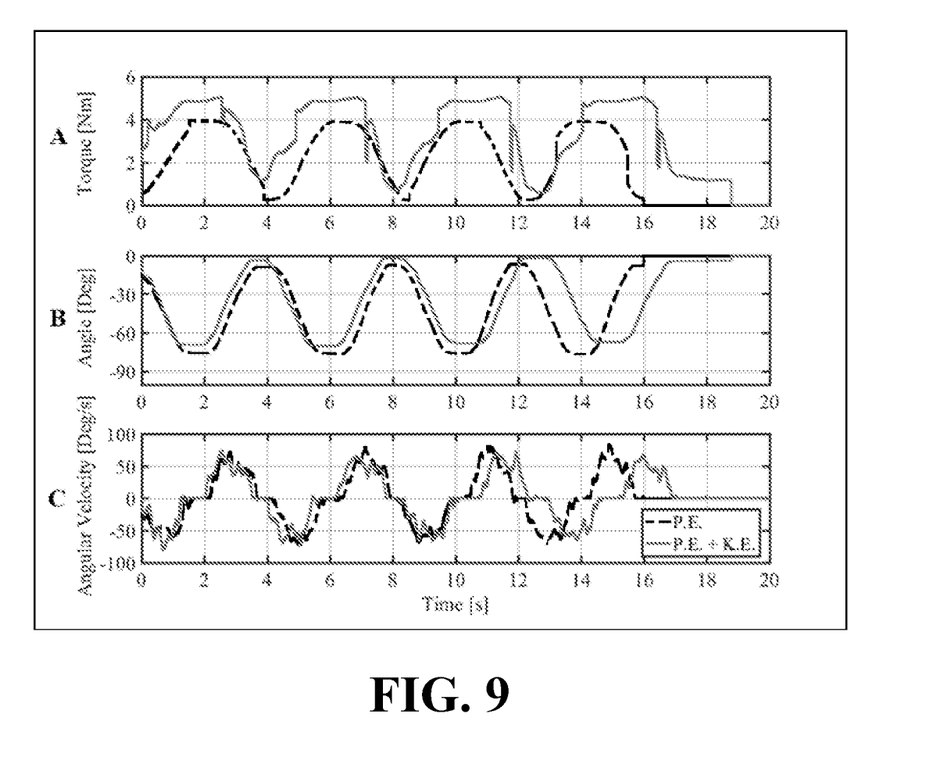
FIG. 9 illustrates a comparison of knee command torques, angles and angular velocities for potential energy and total energy shaping during STS transitions.

FIG. 9 shows the results of the experiment pertaining to the knee joint. In particular, FIG. 9 shows a comparison of knee command torques (A), angles (B) and angular velocities (C) for potential energy (P.E., dashed black line) and total energy (P.E.+K.E., solid gray line) shaping during STS transitions. In A, positive torques aid knee extension (negative aid knee flexion). In B, positive angles represent knee extension (negative represent flexion) from the upright standing position (zero degrees). The assistive torques provided by the knee actuator are shown for both modes, as well as the corresponding joint angles and velocities (i.e., sensor feedback to the controller). It is clear that overall, total energy shaping provided higher assistive (extension) torques when compared to the P.E. shaping strategy. With both modes, the highest assistive torques are provided when the subject is seated, i.e., when the knee is the most flexed. Furthermore, the total energy shaping strategy also provides higher torques during the transition phases (periods of acceleration/deceleration) by reducing the perceived inertia. All of the devices, systems and/or methods disclosed and claimed herein can be made and executed without undue experimentation in light of the present disclosure. While the devices, systems and methods of this invention have been described in terms of particular embodiments, it will be apparent to those of skill in the art that variations may be applied to the devices, systems and/or methods in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

Appendix A Satisfying Matching Conditions

Given (5) and (7), the inventors derive the matching condition for the ECD and separate it into sub-matching conditions that correspond to matching for kinetic and potential energy and human inputs, respectively:

$$B_\lambda^\perp [C_\lambda \dot{q} + N_\lambda + M_\lambda \tilde{M}_\lambda^{-1}(\tilde{C}_\lambda \dot{q} + \tilde{N}_\lambda)] = 0, \quad (18)$$

$$B_\lambda^\perp [B_\lambda v + J_\lambda^T F - M_\lambda \tilde{M}_\lambda^{-1}(\tilde{B}_\lambda v + \tilde{J}_\lambda^T F)] = 0, \quad (19)$$

Matching for Kinetic and Potential Energy Prior research showed that the bottom-right submatrix of a mass matrix is the mass matrix of a lower-dimensional mechanical system [48]. This motivates the inventors to shape the bottom-right part in $M_\lambda$, which may render matching conditions that are easier to satisfy. Following the procedure in [32, 33], one can decompose $M_\lambda$ into matrices blocks, that is, $$M = \begin{bmatrix} M_1 & M_2 \\ M_2^T & M_4 \end{bmatrix} = M_\lambda, \quad (20)$$

where $M_1 \in \mathbb{R}^{c \times c}$, $M_2 \in \mathbb{R}^{c \times (n-c)}$. The inventors want the bottom-right part to be shaped via control, hence the closed-loop inertia matrix is defined as $$\tilde{M} = \begin{bmatrix} M_1 & M_2 \\ M_2^T & \tilde{M}_4 \end{bmatrix} = \tilde{M}_\lambda, \quad (21)$$

where the choice of $\tilde{M}_4$ will be specified in the following sections. Utilizing the relationship between C and M from [26, 52] and the fact that the first c DOFs are constrained, the inventors obtain $$C\dot{q} = D_q \begin{bmatrix} M_2 \dot{q}_{c+1,n} \\ M_4 \dot{q}_{c+1,n} \end{bmatrix} \begin{bmatrix} 0 \\ \dot{q}_{c+1,n} \end{bmatrix} - \frac{1}{2} \partial_q (\dot{q}_{c+1,n}^T M_4 \dot{q}_{c+1,n}),$$

where the subscript (i,j) indicates rows i through j of a matrix. Note that the submatrix $M_4$ does not depend on $q_{1,c}$ based on the recursively cyclic property in [30], yielding simplified expressions for $C\dot{q}$ and $\tilde{C}\dot{q}$ as $$C\dot{q} = \begin{bmatrix} \partial_{q_{c+1,n}}(M_2 \dot{q}_{c+1,n}) \dot{q}_{c+1,n} \\ \Psi \end{bmatrix}, \quad (22)$$

$$\tilde{C}\dot{q} = \begin{bmatrix} \partial_{q_{c+1,n}}(M_2 \dot{q}_{c+1,n}) \dot{q}_{c+1,n} \\ \tilde{\Psi} \end{bmatrix}, \text{ where} \quad (23)$$

$$\Psi := \frac{1}{2} \partial_{q_{c+1,n}} (\dot{q}_{c+1,n}^T M_4 \dot{q}_{c+1,n}) \in \mathbb{R}^{(n-c) \times 1},$$

$$\tilde{\Psi} := \frac{1}{2} \partial_{q_{c+1,n}} (\dot{q}_{c+1,n}^T \tilde{M}_4 \dot{q}_{c+1,n}) \in \mathbb{R}^{(n-c) \times 1}.$$

Multiplying $(I-A^T W A M^{-1})$ with (22) and $(I-A^T \tilde{W} A \tilde{M}^{-1})$ with (23), the inventors obtain $$C_\lambda \dot{q} = \begin{bmatrix} Y\Psi \\ \Psi \end{bmatrix}, \tilde{C}_\lambda \dot{q} = \begin{bmatrix} \tilde{Y}\tilde{\Psi} \\ \tilde{\Psi} \end{bmatrix}, \quad (24)$$

where $Y = M_2 M_4^{-1}$ and $\tilde{Y} = M_2 \tilde{M}_4^{-1}$. Similarly, the constrained potential forces vectors can be calculated as $$N_\lambda = \begin{bmatrix} Y N_{c+1,n} \\ N_{c+1,n} \end{bmatrix}, \tilde{N}_\lambda = \begin{bmatrix} \tilde{Y} \tilde{N}_{c+1,n} \\ \tilde{N}_{c+1,n} \end{bmatrix}, \quad (25)$$

where the choices of desired gravitational forces vector $\tilde{N}_{c+1,n}$ will be specified later.

To simplify the multiplication between $M_\lambda$ and $\tilde{M}_\lambda^{-1}$, the inventors apply the blockwise inversion method again to obtain $$M_\lambda \tilde{M}_\lambda^{-1} = \begin{bmatrix} I_{c \times c} & 0_{c \times (n-c)} \\ \Omega_1 & \Omega_2 \end{bmatrix}, \quad (26)$$

where $\Omega_1 = (I - M_4 \tilde{M}_4^{-1}) M_2^T (M_1 - M_2 \tilde{M}_4^{-1} M_2^T)^{-1} \in \mathbb{R}^{(n-c) \times c}$ and $\Omega_2 = -\Omega \tilde{Y} + M_4 \tilde{M}_4^{-1} \in \mathbb{R}^{(n-c) \times (n-c)}$. The matrix $B_\lambda$ is calculated from (6) and its annihilator $B_\lambda^\perp$ can be chosen as $$B_\lambda = \begin{bmatrix} YB_{c+1,n} \\ B_{c+1,n} \end{bmatrix}, B_\lambda^\perp = \begin{bmatrix} I_{c \times c} & -Y \\ 0_{(n-p-c) \times c} & S \end{bmatrix}, \quad (27)$$

where $S = [I_{(n-p-c) \times (n-p-c)}, 0_{(n-p-c) \times p}]$. When the system is fully-constrained, that is, $n = p + c$, the second block row of the annihilator disappears. It can be verified that $B_\lambda^\perp \in \mathbb{R}^{(n-p) \times n}$, $\text{rank}(B_\lambda^\perp) = n-p$, and $B_\lambda^\perp B_\lambda = 0_{(n-p) \times p}$.

Plugging $B_\lambda^\perp$, (24), (25), and (26) into (18), the left-hand side of the matching condition becomes $$B_\lambda^\perp [C_\lambda \dot{q} + N_\lambda - M_\lambda \tilde{M}_\lambda^{-1}(\tilde{C}_\lambda \dot{q} + \tilde{N}_\lambda)] = \begin{bmatrix} I_{c \times c} & -Y \\ 0_{(n-p-c) \times c} & S \end{bmatrix} \begin{bmatrix} Y\xi - \tilde{Y}\tilde{\xi} \\ \xi - \Omega_1 \tilde{Y}\tilde{\xi} - \Omega_2 \tilde{\xi} \end{bmatrix}, \quad (28)$$

where $\xi = \Psi + N_{c+1,n}$ and $\tilde{\xi} = \tilde{\Psi} + \tilde{N}_{c+1,n}$. The first $c$ rows of (28) can be simplified as $$[I_{c \times c} \quad -Y] \begin{bmatrix} Y\xi - \tilde{Y}\tilde{\xi} \\ \xi - \Omega_1 \tilde{Y}\tilde{\xi} - \Omega_2 \tilde{\xi} \end{bmatrix} = (-\tilde{Y} + Y\Omega_1 \tilde{Y} + Y\Omega_2)\tilde{\xi} = \quad (29)$$

$$(-\tilde{Y} + YM_4 \tilde{M}_4^{-1})\tilde{\xi} = (-\tilde{Y} + M_2 \tilde{M}_4^{-1})\tilde{\xi} = 0_{c \times 1}.$$

For contacts (for example, heel or toe contact) that result in underactuation ($n > p + c$), additional analysis is needed to fully satisfy the matching condition (18), that is, the bottom $(n-p-c)$ rows of (28) must also be satisfied.

Note that during underactuated cases, $M_4$ cannot be shaped arbitrarily. The inventors propose satisfying the matching condition by shaping only the bottom-right $p \times p$ part of $M_4$, which is associated with the $p$ actuated coordinates. To show this, the inventors first decompose and shape $M_4$ in a similar manner to (21) as $$M_4 = \begin{bmatrix} M_{41} & M_{42} \\ M_{42}^T & M_{44} \end{bmatrix}, \tilde{M}_4 = \begin{bmatrix} M_{41} & M_{42} \\ M_{42}^T & \tilde{M}_{44} \end{bmatrix},$$

where $M_{41} \in \mathbb{R}^{(n-p-c) \times (n-p-c)}$, $M_{42} \in \mathbb{R}^{(n-p-c) \times p}$, and $M_{44} \in \mathbb{R}^{p \times p}$. Similar to (26), the top-left element of $M_4 \tilde{M}_4^{-1}$ will be $I_{(n-p-c) \times (n-p-c)}$. Subtracting $M_4 \tilde{M}_4^{-1}$ from $I_{(n-c) \times (n-c)}$, the first $(n-p-c)$ rows of $\Omega_1$ will become zeroes. As a consequence, the first $(n-p-c)$ rows of $\Omega_2$ become $[I_{(n-p-c) \times (n-p-c)}, 0_{(n-p-c) \times p}]$. Leveraging these properties of $\Omega_1$ and $\Omega_2$, the bottom $(n-p-c)$ rows of (28) become $$[0_{(n-p-c) \times c} \quad S] \begin{bmatrix} Y\xi - \tilde{Y}\tilde{\xi} \\ \xi - \Omega_1 \tilde{Y}\tilde{\xi} - \Omega_2 \tilde{\xi} \end{bmatrix} = \quad (30)$$

$$\frac{1}{2} \partial_{q_{c+1,n-p}} (\dot{q}_{c+1,n}^T (M_4 - \tilde{M}_4) \dot{q}_{c+1,n}) + N_{c+1,n-p} - \tilde{N}_{c+1,n-p}.$$

From [48], the inventors know $\partial M_{44}/\partial q_{c+1,n-p} = 0$, i.e., $q_{c+1,n-p}$ is cyclic in $M_{44} \in \mathbb{R}^{p \times p}$. Utilizing this fact and assuming $N_{c+1,n-p} = \tilde{N}_{c+1,n-p}$ (the rows that correspond to the unactuated DOFs that are unconstrained), (30) equals $0_{(n-p-c) \times 1}$ and the matching condition (18) is satisfied.

Matching for Human Inputs

Because the human joint input $v$ and the interaction forces $F$ are not easily measured in practice, the inventors choose the closed-loop mappings $\tilde{B}$ and $\hat{J}^T$ such that $v$ and $F$ disappear from the exoskeleton control law and the matching condition (19) is satisfied. In particular, the inventors solve the equations $B_\lambda^\perp(B_\lambda - M_\lambda \tilde{M}_\lambda^{-1} \tilde{B}_\lambda) = 0$ and $B_\lambda^\perp(J_\lambda^T - M_\lambda \tilde{M}_\lambda^{-1} \hat{J}_\lambda^T) = 0$ for $$\tilde{B}_{c+1,n} = \tilde{M}_4 M_4^{-1} B_{c+1,n}) \quad (31)$$

$$\hat{J}_{c+1,n}^T = \tilde{M}_4 M_4^{-1} J_{c+1,n}^T. \quad (32)$$

These terms immediately satisfy the matching condition (19) and alter the way that the human joint inputs $v$ and interaction forces $F$ enter the closed-loop system dynamics. Given (31) and (32), the control law that brings (5) into (7) becomes $$u = (B_\lambda^T B_\lambda)^{-1} B_\lambda^T [C_\lambda \dot{q} + N_\lambda - M_\lambda \tilde{M}_\lambda^{-1}(\tilde{C}_\lambda \dot{q} + \tilde{N}_\lambda)]. \quad (33)$$

REFERENCES

The contents of the following references are incorporated by reference herein:

[1] T. Yan, M. Cempini, C. M. Oddo, and N. Vitiello, "Review of assistive strategies in powered lower-limb orthoses and exoskeletons," *Rob. Auton. Syst*, vol. 64, pp. 120-136, 2015.

[2] G. Zeilig, H. Weingarden, M. Zwecker, I. Dudkiewicz, A. Bloch, and A. Esquenazi, "Safety and tolerance of the ReWalk™ exoskeleton suit for ambulation by people with complete spinal cord injury: A pilot study," *The Journal of Spinal Cord Medicine*, vol. 35, no. 2, pp. 96-101, 2012.

[3] S. A. Murray, K. H. Ha, C. Hartigan, and M. Goldfarb, "An assistive control approach for a lower-limb exoskeleton to facilitate recovery of walking following stroke," *IEEE Trans. Neural Syst. Rehabil. Eng.*, vol. 23, no. 3, pp. 441-449, 2015.

[4] R. Jimenez-Fabian and O. Verlinden, "Review of control algorithms for robotic ankle systems in lower-limb orthoses, prostheses, and exoskeletons," *Medical Engineering &Physics*, vol. 34, no. 4, pp. 397-408, 2012.

[5] R. D. Gregg, T. Lenzi, L. J. Hargrove, and J. W. Sensinger, "Virtual constraint control of a powered prosthetic leg: From simulation to experiments with transfemoral amputees," *IEEE Trans. Rob.*, vol. 30, no. 6, pp. 1455-1471, 2014.

[6] D. Quintero, D. J. Villarreal, D. J. Lambert, S. Kapp, and R. D. Gregg, "Continuous-phase control of a powered knee {ankle prosthesis: Amputee experiments across speeds and inclines," *IEEE Trans. Rob.*, 2018, in press.

[7] A. Duschau-Wicke, T. Brunsch, L. Lunenburger, and R. Riener, "Adaptive support for patient-cooperative gait rehabilitation with the Lokomat," in Intelligent Robots and Systems, 2008. IROS 2008. *IEEE/RSJ International Conference on. IEEE,* 2008, pp. 2357-2361.

[8] R. Ortega, J. A. L. Perez, P. J. Nicklasson, and H. Sira-Ramirez, *Passivity-Based Control of Euler-Lagrange Systems: Mechanical, Electrical and Electromechanical Applications.* Berlin, Germany: Springer Science, 1998.

[9] R. Ortega, A. J. Van der Schaft, I. Mareels, and B. Maschke, "Putting energy back in control," *IEEE Control Syst. Mag., vol.* 21, no. 2, pp. 18-33, 2001.

[10] G. Blankenstein, R. Ortega, and A. J. Van Der Schaft, "The matching conditions of controlled Lagrangians and IDA-passivity based control," *Int. J Control,* vol. 75, no. 9, pp. 645-665, 2002.

[11] R. Ortega, M. W. Spong, F. Gomez-Estern, and G. Blankenstein, "Stabilization of a class of underactuated mechanical systems via interconnection and damping assignment," *IEEE Trans. Automat. Contr.,* vol. 47, no. 8, pp. 1218-1233, 2002.

[12] A. M. Bloch, D. E. Chang, N. E. Leonard, and J. E. Marsden, "Controlled Lagrangians and the stabilization of mechanical systems II: Potential shaping," *IEEE Trans. Automat. Contr.,* vol. 46, no. 10, pp. 1556-1571, 2001.

[13] R. D. Gregg and M. W. Spong, "Reduction-based control with application to three-dimensional bipedal walking robots," in 2008 *Am. Control Conf. IEEE,* 2008, pp. 880 {887.

[14] R. D. Gregg and M. W. Spong, "Bringing the compass-gait bipedal walker to three dimensions," in 2009 *IEEE/RSJ Int Conf. Intell. Robot. Syst.* IEEE, 2009, pp. 4469-4474.

[15] R. D. Gregg and M. W. Spong, "Reduction-based control of branched chains: Application to three dimensional bipedal torso robots," in *Decision and Control,* 2009 *held jointly with the* 2009 *28th Chinese Control Conference. CDC/CCC* 2009. *Proceedings of the 48th IEEE Conference on.* IEEE, 2009, pp. 8166-8173.

[16] A. D. Ames and R. D. Gregg, "Stably extending two-dimensional bipedal walking to three dimensions," in *American Control Conference (ACC),* 2007. IEEE, 2007, pp. 2848-2854.

[17] A. D. Ames, R. D. Gregg and M. W. Spong, "A geometric approach to three-dimensional hipped bipedal robotic walking," in *Decision and Control,* 2007 *46th IEEE Conference on.* IEEE, 2007, pp. 2848-2854.

[18] R. D. Gregg, Y. Y. Dhaher, A. Degani, and K. M. Lynch, "On the mechanics of functional asymmetry in bipedal walking," *IEEE Trans. Biomed. Eng,* vol. 59, no. 5, pp. 1310-1318, 2012.

[19] T. McGeer et al., "Passive dynamic walking," *I. J Robotic Res.,* vol. 9, no. 2, pp. 62-82, 1990.

[20] A. Goswami, B. Thuilot, and B. Espiau, "Compass-like biped robot part I: Stability and bifurcation of passive gaits," Institut National de Rechercheen Informatique et en Automatique (INRIA), Grenoble, France, Tech. Rep. 2996, 1996.

[21]--, "A study of the passive gait of a compass-like biped robot: Symmetry and chaos," *Int. J. Robot. Res.,* vol. 17, no. 12, pp. 1282-1301, 1998.

[22] S. H. Collins, M. Wisse, and A. Ruina, "A three-dimensional passive dynamic walking robot with two legs and knees," *Int. J. Rob. Res.,* vol. 20, no. 7, pp. 607-615, 2001.

[23] M. W. Spong, "The passivity paradigm in bipedal locomotion," in *Proceedings of the International Conference on Climbing and Walking Robots,* Madrid, Spain, 2004.

[24] M. W. Spong and F. Bullo, "Controlled symmetries and passive walking," *IEEE Trans. Autom. Control,* vol. 50, no. 7, pp. 1025-1031, 2005.

[25] J. K. Holm, D. Lee, and M. W. Spong, "Time-scaling trajectories of passive dynamic bipedal robots," in *Robotics and Automation,* 2007 *IEEE International Conference on.* IEEE, 2007, pp. 3603-3608.

[26] J. K. Holm and M. W. Spong, "Kinetic energy shaping for gait regulation of underactuated bipeds," *Proc. IEEE Int. Conf. Control Appl.,* pp. 1232-1238, 2008.

[27] M. W. Spong, J. K. Holm, and D. Lee, "Passivity-based control of bipedal locomotion," *IEEE Rob. Autom. Mag.,* vol. 14, no. 2, pp. 30-40, 2007.

[28] V. de Le'on-G'omez, V. Santibanez, and J. Sandoval, "Interconnection and damping assignment passivity-based control for a compass-like biped robot," *Int. J. Adv. Rob. Syst.,* vol. 14, no. 4, p. 1729881417716593, 2017.

[29] R. D. Gregg, "Geometric control and motion planning for three-dimensional bipedal locomotion," Ph.D. dissertation, University of Illinois at Urbana-Champaign, 2010.

[30] D. Auckly, L. Kapitanski, and W. White, "Control of nonlinear underactuated systems," *Commun. Pure Appl. Math.,* vol. 53, no. 3, pp. 354-369, 2000.

[31] R. D. Gregg, T. W. Bretl, and M. W. Spong, "A control theoretic approach to robot-assisted locomotor therapy," in *Decision and Control (CDC),* 2010 *49th IEEE Conference on.* IEEE, 2010, pp. 1679-1686.

[32] G. Lv and R. D. Gregg, "Orthotic body-weight support through underactuated potential energy shaping with contact constraints," in *Proc. IEEE Conf. Decis. Control,* 2015, pp. 1483-1490.

[33]--, "Underactuated potential energy shaping with contact constraints: Application to a powered knee-ankle orthosis," *IEEE Trans. Control Syst. Technol.,* vol. 26, no. 1, pp. 181-193, 2018.

[34] G. Lv and R. Gregg, "Towards total energy shaping control of lower-limb exoskeletons," in *American Control Conference (ACC),* 2017. IEEE, 2017, pp. 4851-4857.

[35] R. M. Murray, Z. Li, and S. S. Sastry, *A Mathematical Introduction to Robotic Manipulation.* CRC press, 1994.

[36] D. J. Braun, J. E. Mitchell, and M. Goldfarb, "Actuated dynamic walking in a seven-link biped robot," *IEEE/ASME Trans. Mechatron.,* vol. 17, no. 1, pp. 147-156, 2012.

[37] D. J. Braun and M. Goldfarb, "A control approach for actuated dynamic walking in biped robots," *IEEE Trans. Rob.,* vol. 25, no. 6, pp. 1292-1303, 2009.

[38] S. Mochon and T. A. McMahon, "Ballistic walking,"*J. Biomech.,* vol. 13, no. 1, pp. 49-57, 1980.

[39] A. E. Minetti, C. Moia, G. S. Roi, D. Susta, and G. Ferretti, "Energy cost of walking and running at extreme uphill and downhill slopes," *J. Appl. Phycol.,* vol. 93, no. 3, pp. 1039-1046, 2002.

[40] E. R. Westervelt, J. W. Grizzle, and D. E. Koditschek, "Hybrid zero dynamics of planar biped walkers," *IEEE Trans. Autom. Control,* vol. 48, no. 1, pp. 42-56, 2003.

[41] A. Grabowski, C. T. Farley, and R. Kram, "Independent metabolic costs of supporting body weight and accelerating body mass during walking," *J. Appl. Phycol.,* vol. 98, no. 2, pp. 579-583, 2005.

[42] G. Aguirre-Ollinger, J. E. Colgate, M. A. Peshkin, and A. Goswami, "Inertia compensation control of a one-degree-of-freedom exoskeleton for lowerlimb assistance: Initial experiments," *IEEE Trans. Neural Syst. Rehabil. Eng.,* vol. 20, no. 1, pp. 68-77, 2012.

[43] F. Ghorbel, B. Srinivasan, and M. W. Spong, "On the uniform boundedness of the inertia matrix of serial robot manipulators," *Journal of Robotic Systems*, vol. 15, no. 1, pp. 17-28, 1998.

[44] S. L. Kilbreath, S. Perkins, J. Crosbie, and J. McConnell, "Gluteal taping improves hip extension during stance phase of walking following stroke," *Australian Journal of Physiotherapy*, vol. 52, no. 1, pp. 53-56, 2006.

[45] S. H. Collins, M. B. Wiggin, and G. S. Sawicki, "Reducing the energy cost of human walking using an unpowered exoskeleton," *Nature*, vol. 522, no. 7555, pp. 212-215, 2015.

[46] A. Silder, T. Besier, and S. L. Delp, "Predicting the metabolic cost of incline walking from muscle activity and walking mechanics,"*J. Biomech.*, vol. 45, no. 10, pp. 1842-1849, 2012.

[47] A. E. Martin and J. P. Schmiedeler, "Predicting human walking gaits with a simple planar model,"*J. Biomech.*, vol. 47, no. 6, pp. 1416-1421, 2014.

[48] R. D. Gregg and M. W. Spong, "Reduction-based control of three dimensional bipedal walking robots," *Int. J. Rob. Res.*, vol. 29, no. 6, pp. 680-702, 2010.

[49] D. A. Winter, *Biomechanics and Motor Control of Human Movement*. John Wiley & Sons, 2009.

[50] H. Zhu, J. Doan, C. Stence, G. Lv, T. Elery, and R. Gregg, "Design and validation of a torque dense, highly backdrivable powered knee-ankle orthosis," in *Robotics and Automation (ICRA), 2017 IEEE International Conference on*. IEEE, 2017, pp. 504-510.

[51] R. Krishnan, *Permanent magnet synchronous and brushless DC motor drives*. CRC press, 2009.

[52] J. Holm, "Gait regulation for bipedal locomotion," Ph.D. dissertation, University of Illinois at Urbana-Champaign, 2008.

[53] Muscle strength and weight-bearing symmetry relate to sit-to-stand performance in individuals with Stroke, Lomaglio, Melanie J. et al., Gait & Posture, Volume 22, Issue 2, 126-131.

The invention claimed is:

1. An orthosis device comprising:
    a first support member;
    a second support member;
    a plurality of sensors configured to measure a plurality of parameters, wherein the plurality of parameters includes:
        an angle between the first support member and the second support member; and
        an orientation of the first support member or the second support member;
    an actuator configured to apply a torque to the first or second support member; and
    a controller, wherein:
        the controller is configured to calculate a plurality of forces exerted on a person coupled to the orthosis device, wherein:
            the plurality of forces include an inertial force and a gravitational force; and
            the plurality of forces are calculated based on the angle between the first support member and the second support member and based on the orientation of the first support member or the second support member;
        the controller is configured to control the torque applied by the actuator; and
        the torque applied by the actuator is controlled to:
            counteract the plurality of forces exerted on the person and device, wherein:
                the plurality of forces exerted on the person and the device include an inertial force exerted on the person and the device; and
                the plurality of forces exerted on the person and the device include a gravitational force exerted on the person and the device;
            compensate for lower-limb inertia via kinetic energy shaping; and
            provide body weight support via potential energy shaping.

2. The orthosis device of claim 1 wherein the plurality of sensors includes an inertial measurement unit (IMU) coupled to the first support member or the second support member.

3. The orthosis device of claim 1 wherein the plurality of sensors includes a joint encoder configured to measure the angle between the first support member and the second support member.

4. The orthosis device of claim 3 wherein the joint encoder is an optical encoder.

5. The orthosis device of claim 3 wherein the joint encoder is a magnetic encoder.

6. The orthosis device of claim 1 wherein the torque applied by the actuator is kinetically controlled via a non-linear control method.

7. The orthosis device of claim 1 wherein the actuator comprises an electric motor, and wherein the controller is configured to vary an electric current to the electric motor.

8. The orthosis device of claim 1 wherein:
    the first support member is configured to be coupled to a shin of a person;
    the second support member is configured to be coupled to a thigh of a person; and
    the actuator is configured to vary the angle between the first support member and the second support member.

9. The orthosis device of claim 1 wherein:
    the first support member is configured to be coupled to a thigh of a person; and
    the second support member is configured to be coupled to a hip of a person; and
    the actuator is configured to vary the angle between the first support member and the second support member.

10. The orthosis device of claim 1 wherein:
    the first support member is configured to be placed under a foot of a person;
    the second support member is configured to be coupled to a shin of a person; and
    the actuator is configured to vary the angle between the first support member and the second support member.

11. The orthosis device of claim 10 wherein the plurality of sensors comprises a first sensor in the first support member configured to measure a force in a ball area of the foot of the person.

12. The orthosis device of claim 11 wherein the plurality of sensors comprises a second sensor in the first support member configured to measure a force in a heel area of the foot of the person.

13. The orthosis device of claim 1 wherein:
    the actuator comprises an electric motor coupled to a gearbox and a first sprocket;
    the orthosis device comprises a second sprocket coupled to the first support member; and
    the orthosis device comprises a belt coupling the first sprocket and the second sprocket.

14. The orthosis device of claim 13 further comprising a reaction torque sensor coupled to the gearbox.

15. The orthosis device of claim 14 wherein the gearbox comprises a planetary gear transmission, and wherein the reaction torque sensor is configured to measure torque at an end of the planetary gear transmission.

16. The orthosis device of claim 1 wherein the orthosis device comprises:
   an electric motor, a first sprocket, a second sprocket, a belt and a gearbox, wherein:
      the electric motor is coupled to the first sprocket;
      the belt couples the first sprocket and the second sprocket; and
      the gearbox is located inside the second sprocket.

17. The orthosis device of claim 16 wherein the gearbox is configured to be coupled to a joint of a person.

18. The orthosis device of claim 1 wherein the orthosis device comprises:
   an electric motor and a gearbox, wherein:
      the electric motor is directly coupled to the gearbox.

19. The orthosis device of claim 18 wherein the gearbox is a single-stage planetary gearbox.

20. The orthosis device of claim 19 wherein the gearbox is configured to be coupled to a joint of a person.

21. A method for controlling an orthosis device coupled to a person, the method comprising:
   measuring a plurality of parameters, wherein:
      the orthosis device comprises a first support member, a second support member, an actuator and a controller; and
      the plurality of parameters includes:
         an angle between the first support member and the second support member; and
         an orientation of the first support member or the second support member;
   applying a torque to one of the plurality of support members via the actuator; and
   controlling the torque applied via the actuator, wherein:
      the torque applied via the actuator is controlled to counteract a plurality of forces exerted on the person and the orthosis device;
      the plurality of forces exerted on the person and the device include an inertial force exerted on the person and the device; and
      the plurality of forces exerted on the person and the device include a gravitational force exerted on the person and the device;
      torque applied via the actuator is not controlled to direct the orthosis device in a pre-determined pattern of motion;
      the torque applied via the actuator is controlled to compensate for lower-limb inertia via kinetic energy shaping; and
      the torque applied via the actuator is controlled to provide body weight support via potential energy shaping.

22. The method of claim 21 wherein the orientation of the first support member or the second support member is measured via an inertial measurement unit (IMU).

23. The method of claim 21 wherein the angle between the first support member and the second support member is measured via an optical encoder.

24. The method of claim 21 wherein the torque is kinetically controlled via a nonlinear control method.

25. The method of claim 21 wherein the actuator comprises an electric motor, and wherein the controller varies an electric current to the electric motor to control the torque applied via the actuator.

26. The method of claim 21 wherein:
   the first support member is coupled to a shin of a person;
   the second support member is coupled to a thigh of a person; and
   the actuator varies the angle between the first support member and the second support member.

27. The method of claim 21 wherein:
   the first support member is placed under a foot of a person;
   the second support member is coupled to a shin of a person; and
   the actuator varies the angle between the first support member and the second support member.

28. The method of claim 27 wherein:
   the plurality of sensors comprises a first sensor in the first support member; and
   the first sensor in the first support member measures a force in a ball area of the foot of the person.

29. The method of claim 28 wherein:
   the plurality of sensors comprises a second sensor in the first support member; and
   the second sensor in the first support member measures a force in a heel area of the foot of the person.

30. The method of claim 21 wherein:
   the actuator comprises an electric motor coupled to a gearbox and a first sprocket;
   the orthosis device comprises a second sprocket coupled to the first support member; and
   the orthosis device comprises a belt coupling the first sprocket and the second sprocket.

31. The method of claim 30 wherein the orthosis device comprises a reaction torque sensor coupled to the gearbox.

32. The method of claim 30 wherein the gearbox comprises a planetary gear transmission, and wherein the reaction torque sensor measures torque at an end of the planetary gear transmission.

* * * * *